United States Patent [19]

Lin

[11] Patent Number: 4,789,745

[45] Date of Patent: Dec. 6, 1988

[54] CERTAIN 3-[3-(3-PYRIDINYLOXY)PROPOXY OR PROPYLTHIO]-ACETIC ACID DERIVATIVES WHICH ARE USEFUL AS SYNTHETASE INHIBITORS

[75] Inventor: Chiu-Hong Lin, Portage, Mich.

[73] Assignee: The Upjohn Company, Kalamazoo, Mich.

[21] Appl. No.: 110,632

[22] Filed: Oct. 16, 1987

Related U.S. Application Data

[63] Continuation of Ser. No. 774,374, Sep. 9, 1985, abandoned, which is a continuation of Ser. No. 399,141, Jul. 16, 1982, abandoned.

[51] Int. Cl.[4] .............................. C07D 213/65
[52] U.S. Cl. ..................... 546/301; 546/300; 546/334; 546/341; 546/344
[58] Field of Search .......................... 546/341, 301

[56] References Cited

U.S. PATENT DOCUMENTS 2,559,546  7/1951  Perkins ................... 546/301
4,112,224  9/1978  Bundy ..................... 544/131

FOREIGN PATENT DOCUMENTS 2039903A  7/1979  United Kingdom ............... 546/301
2068950   8/1981  United Kingdom ............... 546/341

OTHER PUBLICATIONS

D. Harris, et al., Advances in Prostaglandin and Thromboxane Research 6:437 (1980).
T. Miyamoto, et al., Advances in Prostaglandin and Thromboxane Research 6:443 (1980).
H. Tai, et al., Advances in Prostaglandin and Thromboxane Research 7:447 (1980).
Leardini, et al., Synthesis 3:225 (1982).
Kamiya, Chem. Pharm. Bull. 23:2744 (1975).
Rovier, et al., Bull. Soc. Chim. Fr. 5:1717, 1718 (1971).
Chem. Abstracts, Tenth Collective Index, Chem. Substances 3H-Pyrazole-Questran, p. 46, 178CS (1981).
Tanouchi et al., Chem. Abstracts, vol. 95 (15), Abst. No. 95:125,868g, Oct. 12, 1981.

*Primary Examiner*—Alan L. Rotman
*Attorney, Agent, or Firm*—Donald L. Corneglio

[57] ABSTRACT

The present invention provides novel ω-(3-pyridynl) oxa-, thia-, and aza- alkanoic acids and esters thereof, which are useful as thromboxane $A_2$ ($TXA_2$) inhibitors and as such represent potent pharmacological agents.

4 Claims, No Drawings

CERTAIN 3-[3-(3-PYRIDINYLOXY)PROPOXY OR PROPYLTHIO]-ACETIC ACID DERIVATIVES WHICH ARE USEFUL AS SYNTHETASE INHIBITORS

CROSS-REFERENCE TO RELATED APPLICATIONS

This application is a continuation of U.S. Ser. No. 774,374, filed Sept. 9, 1985, abandoned, which was a continuation of U.S. Ser. No. 399,141, filed July 16, 1982, abandoned.

DESCRIPTION

1. Background of the Invention

The present invention relates to novel compositions of matter. More particularly, the present invention relates to ω-(3-pyridinyl)oxa, thia-, and aza-alkanoic acids and esters thereof. These compounds are potent thromboxane $A_2$ inhibitors and as such represent useful pharmacological agents.

Since the discovery that human platelets convert the protaglandin endoperoxide ($PGG_2$) into a labile proaggregatory molecule known as thromboxane $A_2$ ($TXA_2$), researchers have sought compounds that could selectively inhibit the biological activity of $TXA_2$. This end may be achieved in two different ways: the synthesis of $TXA_2$ can be blocked by inhibiting the $TXA_2$ synthetase, or a compound could be a receptor level antagonist of $TXA_2$. As therapeutic agents, $TXA_2$ synthetase inhibitors are more useful. See, e.g., R. Gorman, Biological and Pharmacological Evaluation of Thromboxane Synthetase Inhibitors, Advances in Prostaglandin and Thromboxane Research, 6: 417 (1980), and references cited therein.

2. Prior Art

A number of thromboxane inhibitors are known. See for example the bi-heterocyclic 9,11-trideoxy-PGF-type compounds disclosed in U.S. Pat. No. 4,112,224; SQ 80,388 (1-(3-phenyl-2-propenyl)-1H-imidazole) disclosed in D. Harris, et al., Advances in Prostaglandin and Thromboxane Research 6: 437 (1980); pyridine and its derivatives, disclosed in T. Miyamoto, et al., Advances in Prostaglandin and Thromboxane Research 6: 443 (1980), and British patent application No. 2,039,903A (abstracted in Derwent Farmdoc No. 50111C (1980)), see also H. Tai, et al., Advances in Prostaglandin and Thromboxane Research, 6: 447 (1980). Other compounds which have been disclosed as thromboxane synthetase inhibitors include sodium p-benzyl-4(1-oxo-2-(4-chlorobenzyl)-3-phenylpropyl)-phenyl phosphate, imidazoles, nordihydroguaiaretic acid, and 12-hydroperoxy-5,8,10,14-eicosatetraenoic acid (HETE). As noted in the above named British patent specification, however, the inhibitory activity of these latter compounds on thromboxane synthetase is very weak making them unsatisfactory as practically effective medicines.

U.S. Pat. No. 2,559,546 discloses certain 3-pyridoxyalkanoic acids which are stated to be useful as bacteriacides. British patent application 2068950A discloses certain 3-pyridyl-oxy- or -thioalkanoic acids and the like which are stated to be useful as thromboxane synthetase inhibitors. Certain alkyl-N-arylcarbamates are disclosed in Leardini, et al, Synthesis 3: 225 (1982). Kamiya, Chem.. Pharm. Bull. 23: 2744 (1975) discloses N-(3-pyridiyl)methylurethan as an intermediate for certain carcinogenic compounds. Similar compounds, having longer alkyl side chains, are disclosed in Rovier, et al, Bull. Soc. Chim. Fr. 5: 1717, 1718 (1971).

SUMMARY OF THE INVENTION

The present invention particularly provides a compound of the formula I,
wherein $X_1$ is
(a) —O—,
(b) —S—, or
(c) —$NR_2$—;
wherein $Y_1$ is
(a) —O—,
(b) —S—,
(c) —$NR_2$—, or
(d) a valence bond;
wherein $Q_1$ is
(a) —$CH_2OH$, or
(b) —$CO_2R_1$;
wherein $R_1$ is
(a) hydrogen,
(b) a pharmacologically acceptable cation,
(c) ($C_1$–$C_{12}$) alkyl,
(d) $C_3$–$C_{10}$) cycloalkyl,
(e) ($C_7$–$C_{12}$) aralkyl,
(f) phenyl,
(g) phenyl mono-, di-, or trisubstituted by
  (1) chloro,
  (2) ($C_1$–$C_3$) or
  (3) alkyl, or
  (4) phenyl para-substituted by
    (i) —NHCO—$R_{25}$,
    (ii) —O—CO—$R_{26}$,
    (iii) —CO—$R_{24}$,
    (iv) —O—CO—(p—Ph)—$R_{27}$, or
    (v) —CH=N—NH—CO—$NH_2$,
wherein $R_{24}$ is phenyl or acetamidophenyl, $R_{25}$ is methyl, phenyl, acetamidophenyl, benazmidophenyl, or amino, $R_{26}$ is methyl, phenyl, amino or methoxy, $R_{27}$ is hydrogen or acetamido, and —(p—Ph) is 1,4-phenylene;
wherein $R_2$ is
(a) hydrogen,
(b) ($C_1$–$C_5$)alkyl,
(c) —CHO,
wherein m is an integer from 0–6;
  wherein n is an integer from 2–6; and
  wherein p is an integer from 0–6; with the following provisos
(a) m is an integer from 2–6 if $X_1$ is —O— or —S— and $Y_1$ is a valence bond;
(b) p is an integer of from 1–6 if $Y_1$ is a valence bond; and
(c) is not zero when $Y_1$ is other than a valence bond.

The carbon atom content of various hydrocarbon-containing moieties is indicated by a prefix designating the minimum and maximum number of carbon atoms in the moiety, i.e., the prefix ($C_i$-$C_j$) indicates a moiety of the integer "i" to the integer "j" carbon atoms, inclusive. Thus ($C_1$–$C_3$)alkyl refers to alkyl of one to 3 carbon atoms, inclusive, or methyl, ethyl, propyl, and isopropyl.

Examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof.

Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl and cyclodecyl.

Examples of aralkyl of 7 to 12 carbon atoms, inclusive, are benzyl, 2-phenethyl, 1-phenylethyl, 2-phenylpropyl, 4-phenylbutyl, 3-phenylbutyl, 2-(1-naphthylethyl), and 1-(2-naphthylmethyl).

Examples of phenyl substituted by one to 3 chloro or alkyl of one to 3 carbon atoms, inclusive, are p-chlorophenyl, m-chlorophenyl, 2,4-dichlorophenyl, 2,4,6-trichlorophenyl, p-tolyl, m-tolyl, o-tolyl, p-ethylphenyl, 2,5-dimethylphenyl, 4-chloro-2-methylphenyl, and 2,4-dichloro-3-methylphenyl.

The compounds of the present invention may be in the form of pharmacologically acceptable salts. These salts are formed when $R_1$ is a pharmacologically acceptable cation. Such cations include: pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the like aliphatic, cycloaliphatic, araliphatic amines containing up to and including about 18 carbon atoms, as well as heterocyclic amines, e.g., piperidine, morpholine, pyrrolidine, piperazine, and lower-alkyl derivatives thereof, e.g.,
1-methylpiperidine,
4-ethylmorpholine,
1-isopropylpyrrolidine,
2-methylpyrrolidine,
1,4-dimethylpiperazine,
2-methylpiperidine,
and the like, as well as amines containing water-solubilizing or hydrophilic groups, e.g,
mono-, di-, and triethanolamine,
ethyldiethanolamine,
N-butylethanolamine,
2-amino-1-butanol,
2-amino-2-ethyl-1,3-propanediol,
2-amino-2-methyl-1-propanol,
tris(hydroxymethyl)aminomethane,
N-phenylethanolamine,
N-(p-tert-amylphenyl)diethanolamine,
galactamine,
N-methylglycamine,
N-methylglucosamine,
ephedrine,
phenylephrine,
epinephrine,
procaine,
and the like. Further useful amine salts are the basic amino acid salts, e.g.,
lysine and
arginine.

Examples of suitable pharmacologically acceptable quaternary ammonium cations are
tetramethylammonium,
tetraethylammonium,
benzyltrimethylammonium,
phenyltriethylammonium, and the like.

Pharmaceutically acceptable acid addition salts are formed at the pyridinyl moiety and are also useful for administering the compounds of this invention. These salts include hydrochloride, hydrobromide, hydroiodide, sulfate, phosphate, acetate, propionate, lactate, maleate, malate, succinate, tartrate, and the like. They are prepared by methods well known in the art.

The compounds of the present invention will be named herein using the Chemical Abstracts numbering system (see Naming and Indexing of Chemical Substances for Chemical Abstracts during the Ninth Collective Period (1972–1976), a reprint of section IV from the Volume 76 Index Guide.)

The compounds of the present invention are tested for $TXA_2$ inhibitions as follows:

Rabbit aortic strips were superfused in series with Krebs solution. Thromboxane $A_2$ ($TXA_2$) was generated by mixing prostaglandin $H_2$ ($PGH_2$) with human platelet microsomes (HPM).

Potential inhibitors were tested by comparing the response of the rabbit aorta to the amount of $TXA_2$ produced by mixing $PGH_2$ and HPM without the test compound in the reaction medium and then the amount of $TXA_2$ produced when the test compound was added to the HPM 5 minutes before the HPM was mixed with $PGH_2$. By this means compounds which slectively inhibit $TXA_2$ synthetase are found. For a discussion of $TXA_2$ synthetase inhibition testing see, e.g., R. Gorman, supra.

Using this test system, two compounds 3-[3-(3-pyridinyl)propoxy]-pronanoic acid, sodium salt (Example 3) and 6-[Formyl(3-pyridinyl)amino]-hexanoic acid, sodium salt (Example 7), have been shown to be the most effective in inhibiting $TXA_2$ formation. Both compounds have an approximately $ED_{50}$ in this system of between 10 and 100 ng/ml.

The novel compounds of this invention have thus been shown to be highly active as inhibitors of the thromboxane synthetase enzyme system. Accordingly, these novel compounds are useful for administration to mammals, including humans, whenever it is desirable medically to inhibit this enzyme system. For a discussion of the utility of $TXA_2$ inhibitors, see, e.g., Derwent Farmdoc Nos. 18399B; 72896B; 72897B; 634049B; 03755C; 03768C; and 50111C.

Thus, for example, these novel compounds are useful as antiinflammatory agents in mammals and especially humans, and for this purpose, are administered systemically and preferably orally. For oral administration, a dose range of 0.05 to 50 mg per kg of human body weight is used to give relief from pain associated with inflammatory disorders such as rheumatoid arthritis. They are also administered intravenously in aggravated cases of inflammation, preferably in a dose range 0.01 to 100 μg per kg per minute until relief from pain is attained. When used for these purposes, these novel compounds cause fewer and lesser undesirable side effects than do the known synthetase inhibitors used to treat inflammation, for example, aspirin and indomethacin. When these novel compounds are administered orally, they are formulated as tablets, capsules, or as liquid preparations, with the usual pharmaceutical carriers, binders, and the like. For intravenous use, sterile isotonic solutions are preferred.

These compounds are useful whenever it is desired to inhibit platelet aggregation, reduce the adhesive character of platelets, and remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., inravenously, subcutaneously, intramuscularly, and in the form of sterile implants for prolonged action. For rapid response especially in emergency situations, the intravenous route of administration is preferred. Doses in the range about 0.005 to about 20 mg per kg of body weight per day are used, the exact dose depending on the age, weight, and condition of the patient or animal, and on the frequency and route of administration.

These compounds are further useful as additives to blood, blood products, blood substitutes, or other fluids which are used in artificial extracorporeal circulation or perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of these at a total steady state dose of about 0.001 to 10 mg per liter of circulating fluid. It is especially useful to use these compounds in laboratory animals, e.g., cats, dogs, rabbits, monkeys, and rats, for these purposes in order to develop new methods and techniques for organ and limb transplants.

The compounds of the present invention are useful in mammals, including humans and certain useful animals, e.g., dogs and pigs, to reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range about 0.1 µg to about 500 µg/kg of body weight per minute, or in a total daily dose by injection or infusion in the range about 0.1 to about 20 mg/kg of body weight per day, the exact dose depending on the age, weight, and condition of the patient or animal, and on the frequency and route of administration.

The novel compounds are used for the purposes described above in the free acid form, in ester form, and in the pharmacologically acceptable salt form. When the ester form is used, the ester is any of those within the above definition of $R_1$. However, it is preferred that the ester be alkyl of one to 12 carbon atoms, inclusive. Of the alkyl esters, methyl and ethyl are especially preferred for optimum absorption of the compound by the body or experimental animal system; and straight-chain octyl, nonyl, decyl, undecyl, and dodecyl are especially preferred for prolonged activity in the body or experimental animal.

Thromboxane synthetase converts $PGH_2$ (prostaglandin endoperoxide) into $TXA_2$. $PGH_2$ is also converted to prostacyclin, $PGD_2$, and other compounds by other enzymes. Thus, because the compounds of this invention inhibit thromboxane $A_2$ synthetase, they increase the $PGH_2$ substrate and thus increase the amount of endogenous prostacyclin. Therefore, they are also useful for many of the pharmacological purposes for which prostacyclin is employed.

Prostacyclin and a thromboxane synthetase inhibitor have both been shown to be effective in controlling tumor cell metastasis, see, e.g., K. Honn, et al., "Thromboxane Synthetase Inhibitors and Prostacyclin Can Control Tumor Cell Metastasis," an Abstract of the Twentieth Annual Meeting of the American Society for Cell Biolpogy, in the Journal of Cell Biology, 87: 64 (1980).

Similarly, prostacyclin has been shown to be an effective antihypertensive agent. The compounds of the present invention are also used for this purpose. (See, e.g., British patent specification No. 2,039,903A).

For a general discussion of the utility of $TXA_2$ synthetase inhibitors which increase endogenous prostacyclin, see, Aiken, et al. J. Pharmacol. Exp. Ther., 219: 299 (1981).

The compounds of the present invention are prepared by the methods depicted in Charts A, B and C.

In the Charts, $R_{18}$ is an acid hydrolyzable protecting group, $R_{22}$ is ($C_1$–$C_{12}$)alkyl, —OTs represents a tosylate, and $R_{23}$ is amine protecting group such as formyl, acetyl, trifluoroacetyl, or trifluoromethanesulfonyl (J. B. Hendrickson and R. Bergeron, Tetr. Lett., 3839 (1973)) group.

Chart A depicts the synthesis of compounds of the present invention where $X_1$ is —O— and $Y_1$ is a valance bond or —O—.

For the synthesis of compounds wherein $X_1$ is —O— and $Y_1$ is a valance bond, referring to Chart A, a 3-alkanol pyridine of the Formula A-1 is treated with sodium hydride in an inert solvent such as dimethylformamide (DMF). The resulting anion is reacted with an alkyl halide of the formula $Z_1$—$(CH_2)n$-1—C-$(OR_{22})_3$ or $Z_1$—$(CH_2)_{n\text{-}1}$—$COOR_{22}$, wherein $Z_1$ is chloro, bromo, or iodo, to yield a compound of the Formula A-2 or A-3, respectively. Mild acidic hydrolysis of the Formula A-2 compound yields the Formula A-3 compound. Alternatively, an alcohol of the Formula A-1 is alkylated with a halide of the Formula $Z_1$—$(CH_2)_n$—$OR_{18}$ to yield a protected compound of the Formula A-5. Acid hydrolysis of the Formula A-5 compound yields the Formula A-6 compound. Oxidation and esterification of the Formula A-6 compound also gives the Formula A-3 compound. The corresponding pharmacologically acceptable salt may be prepared by means well known in the art, e.g., treatment with sodium hydroxide in methanol to form the sodium salt, to yield the Formula A-4 compound wherein $R_1$ is sodium.

For the synthesis of compounds wherein $X_1$ and $Y_1$ are —O—, referring to Chart A, a 3-alkanol pyridine of the Formula A-1 is converted to the Formula A-5 compound as described above. Mild acid hydrolysis of the Formula A-5 compond yields an alcohol of the Formula A-6. Repeated alkylation of the alcohol of the Formula A-6 compound with a halide of the Formula $Z_1$—$(CH_2)_p$—$COOR_{22}$ yields the Formula A-7 compound of the present invention. Pharmacologically acceptable salts are prepared by methods well known in the art as described above.

Chart B depicts the synthesis of compounds of the present invention wherein $X_1$ is —$NR_2$— and $Y_1$ is —O—, —S—, or —$NR_2$—.

An amine of the Formula B-1 is protected with an amine protecting group by means well known in the art, e.g. a formyl group from formic acid and acetic anhydride, to give a compound of the Formula B-2 wherein $R_{23}$ is —CHO. The amine of the Form B-2 is treated with a halide of the Formula $Z_1$—$(CH_2)_{n-1}$—$COOR_{22}$ and sodium hydride in a solvent such as DMF to yield the Formula B-3 compound of the present invention. Pharmacologically acceptable salts are prepared by methods described above to yield, e.g., the Formula B-5 compound wherein $R_2$ is —CHO and $R_1$ is sodium. Alternatively, this formula B-3 compound wherein $R_{23}$ is formyl group may be hydrolyzed by known methods, e.g. treatment with hydrochloric acid in methanol-water, to give the Formula B-4 compound wherein $R_2$ is hydrogen. Treatment of the Formula B-4 compound with sodium hydroxide in methanol yields the Formula B-5 compound wherein $R_2$ is hydrogen and $R_1$ is sodium. The Formula B-3 compound may be reduced by known methods, e.g. lithium aluminium hydride, to yield the Formula B-6 compound. Alkylation of this Formula B-6 compound by the method depicted in Chart A gives the compounds of the Formulas B-7, B-8, and B-9. Conversion of this Formula B-6 compound with p-toluenesulfonyl chloride in pyridine, as is well known in the art, gives the tosylate of the Formula B-10. Alkylation of the Formula B-10 compound with the anion generated from the thiol derivative of the Formula HS—$(CH_2)_p$—$COOR_{22}$ and base, e.g. methyl mercaptopropionate with sodium methoxide in methanol, yields the sulfide of the Formula B-11 wherein $Y_1$ is —S—. Alkylation of the Formula B-10 compound with the anion generated from the amino derivative of the Formula $HNR_2$—$(CH_2)_p$—$COOR_{22}$ and base, as described above regarding the conversion of the Formula B-2 compound to the Formula B-3 compound, yields the compounds of the Formulas B-11, B-12, and B-13 wherein $Y_1$ is —$NR_2$—.

Chart C depicts the synthesis of compounds of the present invention wherein $X_1$ is —O— or —S— and $Y_1$ is valance bond, —S— or —$NR_2$—.

A compound of the Formula A-4 described in Chart A is treated with p-toluenesulfonyl chloride in pyridine to give the Formula C-1 compound. Alkylation of the Formula C-1 compound with an anion generated from the thio derivative of the Formula HS—$(CH_2)_p$—$COOR_{22}$ and base, as depicted in Chart B, gives the Formulas C-2 and C-3 compounds wherein $Y_1$ is —S—. Alkylation of the Formula C-1 compound with an anion generated from the amino derivative of the Formula $HNR_2$—$(CH_2)_p$—$COOR_{22}$ and base, as depicted in Chart B, gives the Formulas C-2 and C-3 compounds wherein $Y_1$ is —$NR_2$—. A 3-alkanol pyridine of the Formula A-1 is treated with p-toluenesulfonyl chloride in pyridine to yield the Formula C-4 compound. Alkylation of the Formula C-4 compound with an anion generated from the thiol derivative of the Formula HS—$(CH_2)$—$COOR_{22}$ and base, as described above, yields the sulfide of the Formula C-5. The Formula C-5 compound may be reduced and sulfonated to yield the alcohol of the Formula C-6 and the tosylate of the Formula C-7, respectively. Alkylation of the Formula C-7 compound with thiol or amino anions, as described above, gives the Formulas C-8 and C-9 compounds wherein $Y_1$ is —S— or —$NR_2$—, respectively.

$R_{18}$ is a silyl protecting group of the formula —$Si(G_1)_3$. $G_1$ is alkyl of one to 4 carbon atoms, cycloalkyl of 3 to 10 carbon atoms, inclusive, aralkyl of 7 to 12 carbon atoms, inclusive, phenyl, or phenyl substituted with one or 2 fluoro, chloro, or alkyl of one to 4 carbon atoms, with the proviso that in a —$Si(G_1)_3$ moiety the various $G_1$'s are the same or different and at least one $G_1$ is hindered (such as tert-butyl). Silyl groups within the scope of —$Si(G_1)_3$ include dimethylphenylsilyl, triphenylsilyl, t-butyldimethylsilyl, or methylphenylbenzylsilyl. With regard to $G_1$, examples of alkyl are methyl, ethyl, propyl, isobutyl, butyl, sec-butyl, tert-butyl, pentyl, and the like. Examples of aralkyl are benzyl, phenethyl, α-phenylethyl, 3-phenylpropyl, α-maphthylmethyl, and 2-(α-maphthyl)ethyl. Examples of phenyl substituted with halo or alkyl are p-chlorophenyl, m-fluorophenyl, o-tolyl, 2,4-dichlorophenyl, p-tert-butylphenyl, 4-chloro-2-methylphenyl, and 2,4-dichloro-3-methylphenyl. Tert-butyldimethylsilyl is most preferred as a silylating agent.

These silyl groups are known in the art. See for example, Pierce "Silylating of Organic Compounds," Pierce Chemical Company, Rockford Ill. (1968). When silylated products of the charts below are intended to be subjected to chromatographic purification, then the use of silyl groups known to be unstable to chromatography is to be avoided. Further, when silyl groups are to be introduced selectively, silylating agents which are readily available and known to be useful in selective silylations are employed. For example, triphenylsilyl and t-butyldimethylsilyl groups are employed when selective introduction is required. A particularly useful silyl group for this purpose is t-butyldimethylsilyl, although other silyl groups are likewise employed.

Other protective groups within the scope of $R_{18}$ are any group which replaces a hydroxy hydrogen and is neither attacked by nor is as reactive to the reagents used in the transformations used herein as a hydroxy is and which is subsequently replaceable by acid hydrolysis with hydrogen. Several such protective groups are known in the art, e.g., tetrahydropyranyl and substituted tetrahydropyranyl. See for reference E. J. Corey, Proceedings of the Robert A. Welch Foundation Conferences on Chemical Research, XII Organic Synthesis, pgs. 51–79 (1969). Those blocking groups which have been found useful include:

(a) tetrahydropyranyl;
(b) tetrahydrofuranyl; and
(c) a group of the formula —$C(OR_{11})(R_{1-2})$—$CH(R_{13})(R_{14})$, wherein $R_{11}$ is alkyl of one to 18 carbon atoms, inclusive, cycloalkyl of 3 to 10 carbon atoms, inclusive, aralkyl of 7 to 12 carbon atoms, inclusive, phenyl or phenyl substituted wityh one to 3 alkyl of one to 4 carbon atoms, inclusive, wherein $R_{12}$ and $R_{13}$ are alkyl of one to 4 carbon atoms, inclusive, phenyl, phenyl substituted with one, 2, or 3 alkyl of one to 4 carbon atoms, inclusive, or when $R_{12}$ and $R_{13}$ are taken together —$(CH_2)_a$— or when $R_{12}$ and $R_{13}$ are taken together —$(CH_2)_b$—O—$(CH_2)_c$, wherein a is 3, 4, or 5 and b is one, 2 or 3, and c is one, 2, or 3, with the proviso that b plus c is 2, 3, or 4, with the further proviso that $R_{12}$ and $R_{13}$ may be the same or different, and wherein $R_{14}$ is hydrogen or phenyl.

When the blocking group $R_{18}$ is tetrahydropyranyl, the tetrahydropyranyl ether derivative of any hydroxy moieties of the CBA-type intermediates herein is obtained by reaction of the hydroxy-containing compound with 2,3-dihydropyran in an inert solvent, e.g., dichloromethane, in the presence of an acid condensing agent such as p-toluenesulfonic acid or pyridine hydrochloride. The dihydropyran is used in large stoichiometric excess, preferably 4 to 100 times the stiochiometric amount. The reaction is normally complete in less than an hour at 20°-50° C.

When the protective group is tetrahydrofuranyl, 2,3-dihydrofuran is used, as described in the preceding paragraph, in place of the 2,3-dihydropyran.

When the protective group is of the formula —C-($OR_{11}$)($R_{12}$)—CH($R_{13}$)($R_{14}$), wherein $R_{11}$, $R_{12}$, $R_{13}$, and $R_{14}$ are as defined above; a vinyl ether or an unsaturated cyclic or heterocyclic compound, e.g., 1-cyclohexen-1-yl methyl ether, or 5,6-dihydro-4-methoxy-2H-pyran is employed. See C. B. Reese, et al., Journal of the Chemical Society 86, 3366 (1967). The reaction conditions for such vinyl ethers and unsaturated compounds are similar to those for dihydropyran above.

The protective groups as defined by $R_{18}$ are removed by mild acidic hydrolysis. For example, by reaction with (1) hydrochloric acid in methanol; (2) a mixture of acetic acid, water, and tetrahydrofuran, or (3) aqueous citric acid or aqueous phosphoric acid in tetrahydrofuran, at temperatures below 55° C., hydrolysis of the blocking group is achieved.

Certain compounds of the present invention are preferred. Thus, compounds of the Formula I wherein the sum of m+n+p is 2 to 7, $X_1$ is —O— or —NH—, $Y_1$ is valance bond, $Q_1$ is —$CO_2R_1$, $R_1$ is hydrogen, methyl, or a pharmacologically acceptable cation are preferred. Also preferred are compounds of the Formula I wherein the sum of m+n+p is 2 to 7, $X_1$ is —NCHO—, $Y_1$ is —O— or a valence bond, and $R_1$ is hydrogen, methyl, or a pharmacologically acceptable cation.

DESCRIPTION OF THE PREFERRED EMBODIMENTS

The present invention is seen more fully by the Examples given below.

PREPARATION 1

3-Bromo(chloro)-1-propanol, t-Butyldimethylsilyl Ether

Refer to Chart A (preparation of starting material)

3-Bromo-1-propanol (Aldrich Chemical Co.) (25.0 g, 180 mmol) and imidazole (Aldrich Chemical Co.) (36.7 g, 539 mmol) are dissolved in 100 ml dimethylformamide. The stirred solution is placed under a nitrogen atmosphere and cooled to 0° C. While purging the system with nitrogen, t-butyldimethylsilyl chloride (40.7 g, 270 mmol) is added in portions via a powder funnel over 20 min. Upon complete addition the resulting solution is allowed to warm to room temperature and stirred for 17 hr. Again the solution is cooled to 0° C. and 50 ml of water is added. Upon warming to room temperature another 50 ml water is added, the mixture is stirred for 10 min and then diluted with an additional 100 ml water. This mixture is extracted with 500 ml ether and the organic phase is washed with 100 ml 10% aqueous sodium bisulfate, 100 ml saturated aqueous sodium bicarbonate twice with 100 ml brine, dried over $MgSO_4$, filtered and concentrated by atmospheric distillation. The concentrate was distilled at 7 torr collecting a 29.83 g fraction boiling at 61°-68° C. (All distillate boiling below 61° C. is discarded). Analysis of this fraction by gas chromatography (150° C., 6 ft 10% carbowax 20M column) showed the presence of two components in approximately equal amounts (retention times of 0.5 min and 0.7 min, respectively), while the pot residue is essentially comprised of only one component corresponding to the longer retention time component of the major fraction.

The pot residue is redistilled to give 3.23 g of material boiling from 69°-70° C. at 5 torr which corresponded to 3-bromo-1-propanol, t-butyldimethylsilyl ether.

NMR absorptions ($CDCl_3$, TMS, δ) shows peaks observed at 0.08, 0.93, 2.06, 3.55, and 3.77.

The IR absorptions ($\nu$max, film) spectrum reveals peaks at 2950, 2925, 2850, 1470, 1385, 1360, 1255, 1210, 1145, 1100, 1060, 1005, 950, 840, 775 and 665 $cm^{-1}$.

The mass spectrum reveals ions at m/e 197, 195, 169, 167, 153, 139, 137, 115 and 73.

The major fraction (described above) comprised of the two components is redistilled in the hope of separating the two components but no such separation is achieved.

This mixture of the silylated 3-chloro- and 3-bromo-1-propanols is used in the synthesis below without further attempts to separate these components.

PREPARATION 2

3-[3-(3-pyridinyl)propoxy]-1-propanol, t-butyldimethylsilyl ether (Formula I: m is 3, $X_1$ is —O—, n is 2, $Y_1$ is a valance bond, p is zero, $Q_1$ is —$CH_2OR_1$ where $R_1$ is dimethyl-t-butylsilyl)

Refer to Chart A (conversion of A-1 to A-5).

A 250 ml 3-neck oven dried round bottom flask is placed 1.8 g (38 mmol) of a 50% dispersion of sodium hydride in mineral oil. The emulsion is washed 3 times with hexane while stirring the flask under a nitrogen atmosphere to remove the mineral oil. The hexane washes are discarded and the gray solid is suspended in 20 ml dry dimethylformamide (DMF). The flask is equipped with an equalizing pressure addition funnel containing 1.05 g (7.7 mmol) of 3-(3-pyridinyl)-1-propanol, which is added dropwise to the sodium hydrode suspension over 10 min at room temperature. Vigorous bubbling occurs and the resulting mixture is stirred at room temperature for 1 hr. The addition funnel is charged with a solution of 3-bromo(chloro)-1-propanol, t-butyldimethylsilyl ether dissolved in 10 ml of DMF. This solution is added dropwise to the vigorously stirred mixture over 45 min.

After stirring at room temperature under nitrogen for 17 hr the mixture is passed into 100 ml of water and extracted with ether (400 ml). The organic phase is washed 3 times with 100 ml of water, dried over $MgSO_4$, filtered and concentrated in vacuo to give 5.1 g of a yellow oil.

The product was chromatographed on 166 g of silica gel using hexane-acetone (4:1), collecting 40 ml fractions. Fractions 17–25 yield 1.15 g (48%) of the titled product as a yellow oil.

IR (film) peaks are observed at 2950, 2925, 2850, 1570, 1465, 1420, 1255, 1100, 1025, 835, 775, and 715 $cm^{-1}$.

NMR (CDCl$_3$; δ) peaks are observed at 8.55–8.36, 7.73–7.37, 7.14, 3.67, 3.,47, 3.38, 2.68, 2.10–1.50, and 0.88.

EXAMPLE 1

3-[3-(3-pyridinyl)propoxy]-1-propanol (Formula I: m is 3, $X_1$ is —O—, n is 2, $Y_1$ is a valence bond, p is zero, and $Q_1$ is —CH$_2$OH)

Refer to Chart A (conversion of A-5 to A-6).

A round-bottomed flask is charged with 1.15 g (3.7 mmol) of the product of Preparation 2 and 20 ml of HDAc—THF—H$_2$O (3:1:1). The mixture is stirred at room temperature for 24 hr at which time TLC analysis confirms the reaction is complete. The solvent is removed and the crude product mixture is concentrated under reduced pressure. Ethyl acetate is added and the solution is concentrated to remove residual acetic acid. This is repeated several times. The crude product is obtained as a pale-yellow oil.

This product is chromatographed on 55 g of silica gel eluting with hexane-acetone (1:1), and collecting 25 ml fractions. Fractions 18–31 yield 0.69 g (95%) of the titled product.

IR (film) peaks are observed at 3300, 2930, 2855, 1575, 1480, 1420, 1370, 1195, 1175, 1100, 795, and 720 cm$^{-1}$.

NMR (CDCl$_3$, δ) peaks are observed at 8.63–8.32, 7.73–7.45, 7.25, 4.90, 3.78, 3.59, 3.43, 2.72, and 1.85.

EXAMPLE 2

3-[3-(3-pyridinyl)propoxy]-proponic acid, methyl ester (Formula I: m is 3, $X_1$ is —O—, n is 2, $Y_1$ is a valence bond, p is zero, and $Q_1$ is —COOCH$_3$)

Refer to Chart A, (conversion of A-6 to A-3).
Method I

To a magnetically stirred solution of 0.69 g, the product of Example 1 in 50 ml of acetone is treated with 5.0 ml (13 mmol) of Jones reagent. The resulting mixture is stirred at room temperature for 1½ hr at which time no remaining starting material is evident by TLC. Isopropanol is added to quench the excess Jones reagent. To this resulting green colored mixture is added excess etheral diazomethane. Solid NaHCO$_3$ is added to this mixture to basify H (pH 9–10) and the mixture is extracted with ether. The organic extracts are washed with 50 ml of brine. The combined organic layers are washed with brine, dried (Na$_2$SO$_4$), filtered, and concentrated, treated with excess ethereal diazomethane, and concentrated again to give 0.4 g of crude product. This crude product is chromatographed over 55 g of silica gel eluting with hexane-acetone (4:1) and collecting 20 mL fractions. Fractions 7–15 are homogeneous on TLC and are combined and concentrated in vacuo to give 0.104 g of the titled product. To recover more material from the aqueous layer, the aqueous layers of the above work-up are combined and acidified to pH 5–6 and filtered through a pad of Celite. The filtrte is concentrated in vacuo and stirred with THF for 1 hr. The mixture is filtered through Celite again. The solid is washed with additional amount of THF. The filtrate is concentrated again and the resulting solid mixture is diluted with THF and dried over anhydrous Na$_2$SO$_4$. The filtrate is concentrated and purified by chromatography the same way as described above to give additional 0.135 g of the titled product.

IR (film) peaks are observed at 2950, 2860, 1730, 1570, 1475, 1435, 1420, 1365, 1265, 1195, 1110, 1025, 790 and 715 cm$^{-1}$.

NMR (CDCl$_3$, δ) peaks are observed at 8.68–8.35, 7.72–7.42, 7.23, 3.73, 3.72, 3.47, 2.70, 2.60, and 2.15–1.62.

Mass spectral analysis reveals ions at m/e 223.1211, 192, 179, 165, 150, 136, 118, 106, and 93.

The carbon:hydrogen:nitrogen (C:H:N) ratio is 64:11:7.59:6.37.

Method II

A suspension of 2.3 g (48 mmol) of sodium hydride (50% dispersion in mineral oil) is washed three times with hexane under a positive nitrogen atmosphere to remove the mineral oil. The washed hydride is suspended in 50 ml of tetrahydrofuran, stirred for 10 min, and then treated dropwise with a solution of 3-(3-pyridinyl)propanol (Aldrich Chemical Co.) (5.0 g 36 mmol) in 50 ml of tetrahydrofuran over 1.5 min at room temperature under a nitrogen atmosphere. After stirring for 2 hr this mixture is cooled to 0° C., treated dropwise with a solution of ethyl 3-bromopropionate (Aldrich Chemical Co.) (8.2 g, 45 mmol) in 50 ml of tetrahydrofuran, stirred for 1 hr, warmed to room temperature and stirred for 15 min. The reaction is quenched by careful addition of water and tetrahydrofuran is removed under reduced pressure. The concentrate is diluted with 100 ml saturated aqueous sodium bicarbonate and extracted with 300 ml of ethyl acetate. The organic phase is washed twice with 100 ml brine, dried (MgSO$_4$), filtered and concentrated in vacuo to give 6.34 g of crude product as an orange colored oil. This material is chromatographed on 50 g HPLC grade silica gel eluting with hexane-acetone (3:1) and collecting 50 ml fractions. Fractions 5–14 are combined and concentrated in vacuo to give 3.35 g of material. Spectral analysis indicates the major component of this material is the ethyl ester corresponding to the titled product.

This impure material is transesterififed to the methyl ester as described.

The impure ethyl ester is dissolved in 25 ml of methanol, the system is placed under a positibe atmosphere and 0.3 ml (1.3 mmol) of 25% sodium methoxide/methanol is added. After stirring at room temperature for 17 hr TLC analysis confirms the reaction is complete. Saturated aqueous ammonium chloride is added to quench the reaction and methanol is removed under reduced pressure. The residue is diluted with brine and extracted with ethyl acetate. The organic phase is washed with brine, dried (MgSO$_4$), filtered and concentrated in vacuo to give a pale yellow oil. This material is chromatographed on 194 g of HPLC grade silica gel eluting with hexane-acetone (2:1) (+ trace of triethylamine) and collecting 48 ml fractions. Fractions 16–25 are homogeneous by TLC and are combined and concentrated in vacuo to give 1.91 g of pure titled methyl ester. This material is identical to that prepared by Method I.

EXAMPLE 3

3-[3-(3-pyridinyl)propoxy]-propanic acid, Sodium Salt (sodium salt of Example 2)

The product of Example 3 is dissolved in 25 ml of methanol and 8.6 ml (8.60 mmol) of 1N NaOH is then added. The resulting cloudy suspension is stirred at room temperature for 18 hrs at which time TLC analysis confirms that the hydrolysis is complete. The methanol is removed under reduced pressure. The concentrate is diluted with water and filtered through a cotton plug. The filtrate is frozen (dry iceacetone) and lyophilized for 48 hr to give a white granular solid (1.88 g).

PREPARATION 4

3-Bromo-1-propanol, tetrahydropyranyl ether

A solution of 3-bromo-1-propanol (Aldrich Chemical Co.) (73.6 g, 0.529 mol), dihydropyran (102.4 g, 1.2 mol) and 300 mL methylene chloride is treated with 7.4 g of pyridine hydrochloride in portions over 3 min. The resulting solution is stirred at room temperature for 26 hr at which time TLC confirmed the reaction is complete. The solution is poured into 200 ml saturated $NaHCO_3$ and extracted with 600 ml ethyl acetate. The organic phase is washed with 10% aqueous sodium bisulfate, saturated $NaHCO_3$, and brine. Filtered, concentrated, and vacuum distillation (twice) gives 83.0 g (70%) of the titled product (bp 81°–84° C./5 mm).

IR (film) peaks are observed at 2950, 2875, 1440, 1350, 1200, 1135, 1120, 1035, 985, and 870 $cm^{-1}$.

NMR ($CDCl_3$, δ) peaks are observed at 4.74–4.58, 4.16–3.32, and 2.4–1.3.

PREPARATION 5

3-(3-Pyridinyloxy, propoxy tetrahydropyranyl ether

A suspension of 4.7 g (98 mmol) of sodium hydride (50% dispersion in mineral oil) was washed three times with hexane under a nitrogen atmosphere. The hydride was suspended in 60 ml of dimethylformamide (DMF) and stirred for 15 min. A solution of 3-hydroxypyridine (Aldrich Chemical Co.) (6.0 g, 63.1 mmol) in 80 ml of dimethylformamide is added dropwise over a period of 20 min and the resulting mixture is stirred for one hr at room temperature. The mixture is cooled to 0° C. and a solution of 3-bromo-propanol, tetrahydropyranyl ether (17.4 g, 125 mmol) in 60 ml of dimethylformamide is added dropwise over 1 hr and stirred for 1.5 hr. The reaction is quenched by careful dropwise addition of water. The mixture is poured into 100 ml of saturated aqueous sodium bicarbonate and extracted with 600 ml of ether. The organic layer is washed with water, brine, dried $MgSO_4$), filtered and concentrated to give 13.9 g of product.

This product is chromatographed over 194 g of silica gel using 92:1 mixture of hexane:acetone as eluent collected in 43 ml fractions. Fractions 9–17 yield the titled product.

IR (film) 2930, 2860, 1570, 1465, 1420, 1275, 1230, 1195, 1120, 1060, 1030, 970, 900, 870, 800 and 710 $cm^{-1}$.

NMR ($CDCl_3$, δ) peaks are observed at 1.05–2.25, 2.08, 3.53–4.22, 4.56, 7.05–7.27, and 8.10–8.36.

PREPARATION 6

3-(3-Pyridinyloxy)-1-propanol

A round-bottomed flask equipped with a magnetic stirring bar was charged with 2.18 g (9.2 mmol) of the product of Preparation 5, 40 ml of iso-propanol, and 10 ml of 1N HCl. The resulting solution is stirred at room temperature for 8 hr at which time TLC analysis confirms the hydrolysis is complete. The reaction is quenched by the addition of solid sodium bicarbonate. The pH is adjusted to 7–8 and iso-propanol is removed under reduced pressure. The concentrate is poured into 100 ml of saturated sodium bicarbonate and extracted with 500 ml of ethyl acetate. The organic layer is washed with 1N sodium hydroxide, brine, dried over anhydrous magnesium sulfate, filtered and concentrated in vacuo to give a yellow oil.

The product is chromatographed over 50 g of silica gel using a hexane-acetone (1:1) as eluant which is collected in 30 ml fractions. Fractions 11–22 yield 1.11 g of the titled product.

IR (film) peaks are observed at 3300, 2940, 2870, 1565, 1475, 1425, 1275, 1230, 1190, 1060, 990, 955, 800, 710, and 605 $cm^{-1}$.

NMR ($CDCl_3$, δ) peaks are observed at 8.35–8.10, 7.32–7.12, 4.16, 3.87, and 2.34–1.67.

EXAMPLE 4

[3-(3-pyridinyloxy)propoxy]acetic acid, methyl ester (Formula I: m is zero, $X_1$ is —O—, n is 3, $Y_1$ is —O—, P is 1, and $Q_1$ is —$CO_2CH_3$)

Refer to Chart A (conversion of A-6 to A-7).

A 100 ml over dried 2-neck flask, equipped with magnetic stirring bar is charged with 1.0 g (21 mmol) of a 50% sodium hydride emulsion. While sweeping the flask with nitrogen the mixture is washed three times with hexane. The remaining gray powder is suspended in 10 ml dry DMF. The flask is fitted with a 100 ml equalizing pressure addition funnel which is then charged with a solution of 1.11 g (7.2 mmol) of the product of Preparation 6 in 10 ml of DMF. This is added dropwise to the stirred NaH mixture over 10 min at room temperature under a nitrogen atmosphere. After stirring for 2 hr at room temperature the resulting mixture is cooled to 0°–5° C. in an ice bath and a solution of 2.2 g (14 mmol) of methyl bromoacetate in 10 ml of DMF is added dropwise over 10 min. A yellowish-orange suspension results and this suspension is stirred at 0°–5° C. for 2 hr. The reaction is quenched by careful addition of water and the solution is poured into 50 ml saturated $NaHCO_3$. This mixture is extracted with 300 ml ethyl acetate and the organic phase is washed with 100 ml of water, dried over $MgSO_4$, filtered and concentrated to give 1.11 g of an orange colored oil.

The product is chromatographed over 50 g of silica gel using a hexane-acetone (2:1) mixture as eluant, collected in 40 ml fractions. Fractions 6–7 yield 242 mg of titled product as a yellow oil.

NMR absorptions ($CDCl_3$, TMS, δ) spectrum reveals peaks at 8.37–8.13, 7.30–7.13, 4.13, 4.08, 3.72, and 2.10.

The IR spectrum ($\nu$max, film) reveals peaks at 2950, 2875, 1750, 1570, 1470, 1425, 1275, 1220, 1135, 1050, 1010, 800 and 710 $cm^{-1}$.

The mass spectrum shows ions at m/e 225.0999, 198, 185, 166, 152, 146, 131, 122, 108 and 95.

EXAMPLE 5

[3-(3-pyridinyloxy)propoxy]-acetic acid, sodium salt (sodium salt of Example 4)

The ester of Example 4 (0.237 g, 1.053 mmol) is dissolved in 4 ml of methanol. One ml of 1.00N NaOH reagent (1.00 mmol) is added and the resulting solution is stirred for 24 hr at room temperature. TLC analysis still indicates some unhydrolyzed methyl ester and 53 μl of 1.00N NaOH reagent is added and the solution stirred an additional 4 hr. TLC analysis then indicates the hydrolysis is complete and methanol is removed under reduced pressure. The residue is diluted with 10 ml of water and washed with 20 ml of ether. The aqueous phase is frozen and lyophilized for 16 hr to give a yellow amorphous glasslike solid (0.247 g).

NMR absorptions (d$_4$-MeOH; TMS, δ) spectrum reveal peaks at 8.30–8.04, 7.50–7.25, 4.18, 3.86, 3.67, and 2.09.

EXAMPLE 6

6-[Formyl(3-pyridinyl)amino]-hexanoic acid, methyl ester (Formula I: m ix zero, $X_1$ is —N(CHO)—, n is 5, $Y_1$ is a valence bond, p is zero, and $Q_1$ is —$CO_2CH_3$)

Refer to Chart B (conversion of B-1 to B-2 to B-3).

A two-neck flask equipped with a magnetic stirring bar and a dropping funnel is dried and flushed with nitrogen. A 50% emulsion of sodium hydride (6.0 mmol, 288 mg) is placed in the flask and washed twice with dry hexane. To this suspension, 470 mg (5.0 mmol) of 3-amino-pyridine is added and the resulting deep green solution is stirred vigorously. The mixture is stirred until the evolution of bubbles ceases. After 6 hr, 2.09 g (10 mmol) of Br—$(CH_2)_5$—$CO_2CH_3$, and 2.5 ml DMF is added dropwise over 10 min. The solution should be cooled to 0°–5° C. with an ice-bath. The mixture is then stirred at room temperature. The reaction mixture is poured into ice-water and extracted with ethyl acetate. The organic layer is washed with water and then with brine, dried over MgSO$_4$, filtered and concentrated to give a brown oil (1.6 g). After chromatography the NMR (CDCl$_3$, δ) spectra reveals peaks at 8.66–8.43, 7.78–7.26, 8.40, 3.88, 3.68, 2.30, and 1.92–1.10.

The IR spectrum (νmax, film) reveals peaks at 3580, 3450, 3350, 3040, 1735, 1680, 1585, 1575, 1485, 1435, 1360, 1280, 1195, 1180, 1165, 815, and 715 cm$^{-1}$.

The mass spectrum reveals an ion at m/e 250.1317. The C:H:N ratio is 62.01:7.26:10.98.

EXAMPLE 7

6-[Formyl (3-pyridinyl)amino]-hxanoic acid, sodium salt (sodium salt of Example 6)

A round-bottomed flask equipped with a magnetic stirring bar is charged with 666 mg (3.0 mmol) the ester of Example 6 3.15 ml 1N sodium hydroxide, and 9.45 ml methanol. The mixture is stirred at room temperature under a nitrogen atmosphere for 24 hr. The solvent is removed in vacuo to give a yellow solid (680 mg). TLC in ethyl acetate-hexane-ethanol (10:1:1) showed only one spot at the origin.

EXAMPLE 8

6-(3-Pyridinylamino)-hexanoic acid, methyl ester (Formula I: m is zero, $X_1$ is —NH—, n is 5, $Y_1$ is a valence bond, p is zero, and $Q_1$ is —$CO_2CH_3$)

Refer to Chart B (conversion of B-3 to B-4).

A flask equipped with a magnetic stirrer is charged with 450 mg (1.8 mmol) of the product of Example 6, 4.5 ml of 2N HCl and 13.5 ml MeOH. The mixture is stirred at room temperature for 18 hr. The pH of this solution is then adjusted to 5–7 and the methanol is removed under reduced pressure and diazomethane in diethylether-water is added and the mixture is dissolved in 200 ml of theyl acetate. To this mixture 50 ml of saturated NaHCO$_3$ is added and equilibrated in a separatory funnel. The organic layer is washed with brine and dried over MgSO$_4$, filtered and concentrated to the crude product as an oil. This product is purified as in the preceding examples to yield white crystals with a melting point of 60°–61° C. NMR (CDCl$_3$, δ) peaks are observed at 8.04–7.78, 7.26–6.68, 3.95–3.35, 3.66, 3.14, 2.32, and 1.86–1.20.

IR (film) peaks are observed at 3396, 3382, 3039, 3022, 2947, 2928, 2866, 2853, 1724, 1590, 1577, 1519, 1474, 1462, 1652, 1645, and 414 cm$^{-1}$.

EXAMPLE 9

6-(3-Pyridinylamino)-hexanoic acid, sodium salt (sodium salt of Example 8)

Following the procedure of Example 3, the sodium salt of Example 9 is prepared.

PREPARATION 7

2-(3-Pyridinyl)ethanol

A round-bottomed flask equipped with a magnetic stirring bar is charged with 13.9 g (0.08 mol) of (3-pyridinyl)acetic acid, hydrochloride salt (Aldrich Chemical Co.) and 400 ml of tetrahydrofuran (THF) under a nitrogen atmoshphere. To this solution lithium aluminum hydride (6.0 g, 0.16 mol) is added at room temperature for 24 hr. Saturated aqueous sodium sulfate is then added dropwise until the mixture becomes white. The solution is dried over anhydrous sodium sulfate. After filtration and concentration the resulting yellow oil is purified by 324 g of HPLC grade silica gel, eluting with ethyl acetate-hexane-ethanol (10:1:1) and collecting 40 ml fractions. Fractions 21–43 homogeneous on TLC are combined and concentrated in vacuo to give a light yellow oil (3.4 g, 34%).

The NMR (CDCl$_3$, TMS, δ) spectrum shows peaks observed at 8.52–7.08, 3.86 and 2.84.

The IR spectrum (film, νmax) reveals peaks at 3300, 2920, 2860, 1640, 1620, 1590, 1580, 1480, 1420, 1050, 800, and 720 cm$^{-1}$.

The mass spectrum reveals an ion at m/e 123.0681.

PREPARATION 8

Trimethyl ortho-4-bromo-butyrate (Reagent for Example 10) and Trimethyl ortho-5-bromo-pentanoate (Reagent for Example 12)

To a mixture of 74 g of 4-bromo-butyronitrile (Aldrich Chemical Co.), 21 ml of dry methanol, and 250 ml of dry ether at 0° C. under a nitrogen atmosphere is added with efficient stirring 40 g of hydrogen bromide over a 30-min period. The mixture is stirred for an additional 4 hr at 0° C. at which time 100 ml of dry hexane is added. The liquid is removed through a gas-dispersion tube by suction while maintaining a positive nitrogen pressure in the flask. A mixture of 200 ml of each of dry ether and dry hexane is added with stirring and the liquid is again removed by suction.

To the solid residue of imino ester hydrobromide is added 250 ml of dry ether, then 150 ml of dry methanol and 25 ml of methylorthoformate. The mixture is stirred at room temperature for 24 hr. The mixture is cooled to about −10° C. and the solution is decanted from ammonium bromide into a dry nitrogen-filled separatory funnel along with about 100 ml of ether rinse. The organic solution is immediately and quickly washed with an ice-cold solution of 20 g of potassium carbonate and 300 ml of saturated saline (after the initial shaking, some water is added to dissolve precipitated solids). The organic phase is washed with saturated saline, 3 drops of pyridine is added and the solution is then dried briefly over magnesium sulfate. The solution is concentrated in vacuo, 150 ml of benzene is added, and the solution is again concentrated in vacuo. Distillation of the residue gives 66.8 g of product, bp 60°-62° C./0.5 mm.

NMR (CDCl$_3$, TMS, δ) spectrum reveals peaks at 3.50, 3.28, and 1.95.

Trimethyl ortho-5-bromo-pentanoate is prepared by the same procedure as described above starting with 5-bromovalero-nitrile (Aldrich Chemical Co.).

EXAMPLE 10

4-[2-(3-Pyridinyl)ethoxy]-butanoic acid, methyl ester (Formula I: m is 2, X$_1$ is —O—, n is 3, Y$_1$ is a valence bond, p is zero, and Q$_1$ is —COOCH$_3$)

Refer to Chart A (conversion of A-1 to A-2 to A-3).

A 3-neck round-bottomed flask equipped with a magnetic stirring bar is charged with 0.72 g (0.015 mol) of sodium hydride (50% active) under a nitrogen atmosphere. The hydride is washed with dry hexane and suspended in 20 ml of dimethylformamide (DMF). The mixture is cooled to 0°-5° C. and 2-(3-pyridinyl)ethanol (Preparation 7) (1.23 g, 0.01 mol) dissolved in 5 ml of DMF is added dropwise over 10 min. The mixture is stirred at room temperature for 30 min and cooled again to 0°-5° C. A solution of 4.34 g (b 0.015 mol) of trimethyl-4-bromoortholutyrate (Preparation 8) in 5 ml DMF is added dropwise over a period of 30 min. The resulting mixture is stirred at room temperature for 24 hr. Thin-layer chromatography (TLC) shows no starting material remaining. The mixture is treated with water and extracted with ethyl acetate. The organic layer is washed with water, brine, and dried over anhydrous magnesium sulfate. Filtration and concentration afford a yellow oil. This oil is dissolved in 30 ml of methanol and 10 ml of 2N hydrochloric acid and the mixture is stirred at room temperature for 10 min. After treatment with excess saturated aqueous sodium bicarbonate and methanol is removed under reduced pressure. The residue is extracted with ether. The ether layer is washed with water, brine, and dried over anhydrous magnesium sulfate. Filtration and concentration affords a yellow oil. Purification is carried out by using 166 g/HPLC grade silica gel eluting with ethyl acetate-hexane-ethaynol (10:1:1) and collecting 40 ml fractions. Fractions 14–18 are homogeneous on TLC and are combined and concentrated in vacuo to give a yellow oil (0.886 g. 39.7%). The NMR (CDCl$_3$, TMS, δ) spectrum peaks observed are 8.62-7.10, 3.64, 3.62, 2.84, 2.34, and 1.86.

The IR spectrum (film, νmax) reveals peaks at 2940, 1860, 1730, 1570, 1480, 1420, 1360, 1250, 1110, 1040, 1020, 1000, 800, 720, and 630 cm$^{-1}$.

The mass spectrum reveals an ion at 223.1211.

EXAMPLE 11

4-[2-(3-Pyridinyl)ethyl]butanoic Acid, sodium salt (sodium salt of Example 10)

A round bottomed flask equipped with a magnetic stirring bar is charged with 0.715 g (0.0032 mol) of the ester of Example 10. 3.4 ml (0.0034 mol) of 1N sodium hydroxide and 10 ml of methanol. The mixture is stirred under a nitrogen atmosphere at room temperature for 24 hr. TLC shows no starting material remaining. The mixture is lyophilized to give 0.646 g of a light brown solid.

EXAMPLE 12

3-[N-methyl-N-(4-methoxycarbonylbutyl)aminomethyl]pyridine (Formula I: m is 1, X$_1$ is —NCH$_3$—, n is 4, y is a valence bond, p is zero, Q$_1$ is —CO$_2$CH$_3$)

Refer to Chart B (conversion of B-2 to B-3).

A three-neck round bottomed flask with a magnetic stirring bar and a nitrogen inlet, is charged with 2.2 g (0.046 mol) of sodium hydride (50% dispersion in mineral oil). While purging the system with nitrogen the emulsion is washed three times with dry hexane. The remaining gray solid is suspended in 60 ml of DMF and the flask is fitted with a 25 ml equalizing pressure addition funnel. The addition funnel is charged with a solution of 5.6 g (0.046 mol) of 3-(methylaminomethyl)pyridine dissolved oin 26 ml of DMF. This solution is added dropwise over 15 min to the sodium hydride suspension under a nitrogen atmosphere to give a pale purple colored suspension. After stirring for 1 hr the suspension is treated with a solution of trimethyl-5-bromo orthopentanoate in 20 ml of DMF which is added dropwise over 30 min. The resulting mixture is stirred for 3 hrs at which time TLC indicates no remaining starting material. The reaction is quenched by the dropwise addition of water (until gas evaluation ceases) and then poured into 400 ml of ether. The organic phase is washed four times with 100 ml of water, concentrated and then diluted with 50 ml of methanol. Hydrochloric acid (25 ml, 2N) is added and the resulting solution is stirred at room temperature for 15 min. the solution is neutralized by the addition of saturated aqueous sodium bicarbonate and then poured into 100 ml of saturated aqueous sodium bicarbonate. This mixture is extracted with 400 ml of ether and the organic phase is dried over MgSO$_4$, filtered, and concentrated to give 5.07 g of crude product as a yellow oil. The NMR spectrum of this material is consistent for the desired product.

Because of the low recovery (9.68 g of product expected for a 100% conversion) all aqueous washes (from the above workup) are combined and reextracted with 400 ml of ethyl acetate. The organic phase is washed twice with water, (100 ml), dried (MgSO$_4$), filtered and concentrated to give 2.17 g of a brown colored oil. The NMR spectrum indicates this material is the ortho ester of the desired product (unhydrolyzed material).

Again all aqueous washes are combined and concentrated under reduced pressure to a volume of approximately 75 ml. This is combined with the ortho ester of the desired product (unhydrolyzed material) and diluted with 100 ml of methanol and 50 ml of water. Concentrated hydrochloric acid is added dropwise until the pH is lowered to approximately 2. This solution is then stirred at room temperature for 16 hr. Solid sodium bicarbonate is added until the pH is raised to approximately 9 and methanol is removed under reduced pressure. The concentrate is diluted with 100 ml of water and extracted with 400 ml of ethyl acetate. The organic phase is washed twice with water (100 ml), dried (MgSO$_4$), filtered and concentrated to give 1.85 g of crude product as a dark brown oil. This is combined with the previously isolated 5.00 g of crude product (above) and chromatographed on 250 g of silica gel packed in chloroform-ethanol (19:1). Eluting with the packing solvent and collecting 50 ml fractions afford 2.5 g (23%) of pure titled product (fractions 16–30). Fractions 31–50 contain the desired product contaminated with more polar impurities.

The NMR (CDCl$_3$, TMS, δ) spectrum reveals peaks at 8.73–7.23, 3.69, 3.51, 2.56–2.10, and 2.19.

The IR (film, νmax) reveals peaks at 2950, 2794, 1738, 1592, 1577, 1457, 1436, 1427, 1366, 1249, 1199, 1171, 1125, 1027, 861, 834, 789, and 715 cm$^{-1}$.

The mass spectrum reveals ions at m/e 236.1523, 135, and 92.

The C:H:N ratio is 65.29:8.41:11.41.

EXAMPLE 13

Sodium, 3-[N-methyl-N-(4-carboxybutyl)aminomethyl]-pyridine (sodium salt of Example 12)

The ester of Example 12 (1.03 g, 4.36 mmol) is dissolved in 15 ml of methanol. 1N Sodium hydroxide (4.35 ml, 4.35 mmol) is added and the resulting solution is stirred at room temperature for 20 hr. TLC analysis still indicates a trace of unhydrolyzed starting material. Another 0.30 ml of 1N NaOH reagent is added and after stirring an additional 6 hr TLC analysis confirms the hydrolysis is complete. Methanol is removed under reduced pressure and the concentrate is diluted with 50 ml of water. This aqueous solution is washed with ether (organic layer discarded), filtered though a cotton plug, frozen and lyophilized to give 1.05 g of titled product as a yellow granular solid.

EXAMPLE 14

4-[2-(3-Pyridinylethylthio)]-butyric acid, methyl ester (Formula I: m is 2, $X_1$ is —S—, n is 3, $Y_1$ is a valnce bond, p is zero, and Q is —CO$_2$CH$_3$)

Refer to Chart C (conversion of A-1 to C-4 to C-5).

A round-bottomed flask equipped with a magnetic stirring bar is charged with 0.616 g (5.0 mmol) of 2-(3-pyridinyl)ethanol from Preparation 7, 5 ml of pyridine. The mixture is cooled to 0°–5° C. and 1.90 g (10.0 mmol) of p-toluenesulfonyl chloride is added. The resulting mixture is allowed to stand at room temperature for 24 hr. The mixture is then cooled to 0°–5° C. and 0.1 ml of water is added. The mixture is allowed to warm to room temperature and stirred for 30 min. Ethyl acetate is added and the mixture is washed with water, brine, and dried over anyhdrous magnesium sulfate. Filtration and concentration yield the tosylate which is used in the following reaction. A three-neck round-bottomed flask equipped with reflux condenser, gas inlet tube, and stirring bar is charged with 2.04 g (20.0 mmol) of γ-thiolactone (Aldrich Chemical Co.), 1.08 g (20 mmol) of sodium methoxide and 20 ml of methanol. The resulting mixture is stirred at room temperature under a nitrogen atmosphere for 10 min. The tosylate obtained, as described above, dissolved in 20 ml methanol is added and the resulting mixture is stirred at 50° C. for 5 hr. The reaction is quenched with saturated ammonium chloride and methanol is removed under reduced pressure. The concentrate is extracted with ethyl acetate and the organic layer is washed with brine and dried over anhydrous sodium sulfate. Filtration and concentration are followed by column chromatography using silica gel to yield the titled compound.

EXAMPLE 15

4-[2-(3-Pyridinylethylthio)]butyric acid, sodium salt (Formula I: m is 2, $X_1$ is —S—, n is 3, $Y_1$ is a valence bond, p is zero, and $Q_1$ is —CO$_2$Na)

Refer to Chart C (conversion of C-8 to C-9).

The ester of Example 14 is treated with 1.05 equiv. of 1N sodium hydroxide in methanol, as described in Example 5, and the resulting mixture is stirred at room temperature for 24 hr. After the mixture is lyophilized, the sodium salt is obtained.

EXAMPLE 16

[3-(3-Pyridinyl-n-propylthio)]acetic acid, ethyl ester (Formula I: m is 3, $X_1$ is —S—, n is 1, $Y_1$ is a valence bond, p is zero, and $Q_1$ is —CO$_2$Et)

Refer to Chart C (conversion of A-1 to C-4 to C-5).

3-(3-Pyridinyl)propanol (Aldrich Chemical Co.) is converted into the tosylate by the method described in Example 14. Thio anion of ethyl 2-mercaptoacetate (Aldrich Chemical Co.), prepared with sodium hydride in DMF or potassium carbonate in glyme (or acetone), is reacted with the tosylate prepared above. The reaction yields the titled compound after chromatographic purification.

PREPARATION 9

3-Pyridinylmethyl-trifluoromethyl sulfonamide (triflamide)

Refer to Chart B (conversion of B-1 to B-2).

3-Pyridinylmethylamine (Aldrich Chemical Co.) is treated with trifluorosulfonic anhydride [(CF$_3$SO$_2$)$_2$)O] and triethylamine in methylene chloride at −78° C. to give the titled product (J. B. Hendrickson and R. Bergeron, Tetr. Lett., 3839 (1973).

PREPARATION 10

3-Pyridinylmethyl-2-ethyloxy-trifluoromethylsulfonamide (triflamide)

Refer to Chart B (conversion of B-2 to B-3 to B-6).

The title compound of Preparation 8 is alkylated with methyl bromoacetate in acetone (or glyme) using potassium carbonate as base. Using sodium hydride in DMF also gives the alkylation product. The resulting methyl ester is treated with lithium aluminum hydride in THF, as described in Preparation 7, to give the titled product. The purification is carried by either chromatography or crystallization.

EXAMPLE 17

[2-(3-Pyridinylmethylamino)ethyloxy]-acetic acid, methyl ester (Formula I: m is 1, $X_1$ is —NH—, n is 2, $Y_1$ is —O—, p is 1, and $Q_1$ is —CO$_2$CH$_3$)

Refer to Chart B (conversion of B-6 to B-7 to B-8).

The title compound of Preparation 10 is alkylated using methyl bromoacetate, as described in Example 4, to give an o-alkylated triflamide (see reference cited in Preparation 9). Deprotection of triflamide using zinc in acetic acid gives the titled product. Purification is carried out by either chromatography or crystallization.

EXAMPLE 18

[2-(3-Pyridinylmethylamino)ethylthio]-acetic acid, ethyl ester (Formula I: m is 1, $X_1$ is —NH—, n is 2, $Y_1$ is —S—, p is 1, and $Q_1$ is —$CO_2CH_2CH_3$)

Refer to Chart B (conversion of B-6 to B-10 to B-11 to B-12).

The title compound of Preparation 10 is converted into tosylate by the method described in Example 14. This tosylate is then alkylated with thio anion of ethyl 2-mercaptoacetate as described in Example 16. The deprotection of triflamide using zinc in acetic acid, as described in Example 17, gives the titled product. Purification is carried out by either chromatography or crystallization.

PREPARATION 11

Methoxycarbonylmethyl-trifluoromethyl sulfonamide

Glycine methyl ester is treated with trifluorosulfonic anhydride and triethylamine in methylene chloride at $-78°$ C., as described in Preparation 9, gives the titled product.

EXAMPLE 19

[2-(3-Pyridinylmethylamino)ethylamino]-acetic acid, methyl ester (Formula I: m is 1, $X_1$ and $Y_1$ are —NH—, n is 2, p is 1, and $Q_1$ is —$CO_2CH_3$)

Refer to Chart B (conversion of B-6 to B-10 to B-11 to B-12).

The tosylate of Example 18 is alkylated according to the N-alkylation procedure of Preparation 10, to give bis-triflamide. Deprotection of triflamide according to the procedure of Example 17 gives the titled product.

EXAMPLE 20

[3-(3-Pyridinyloxy)-propane-1-thio]-acetic acid, ethyl ester (Formula I: $m_1$ is zero, $X_1$ is —O—, n is 3, $Y_1$ is —S—, p is 1, and $Q_1$ is —$CO_2CH_2CH_3$)

Refer to Chart C (conversion of A-4 to C-1 to C-2).

3-(3-Pyridinyloxy)-1-propanol of Preparation 6 is tosylated with the procedure described in Example 14. The tosylate is alkylated with thio anion according to the procedure described in Example 16 to give the titled product.

FORMULA

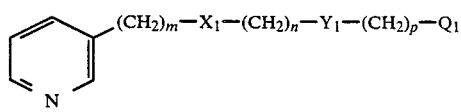

CHART A

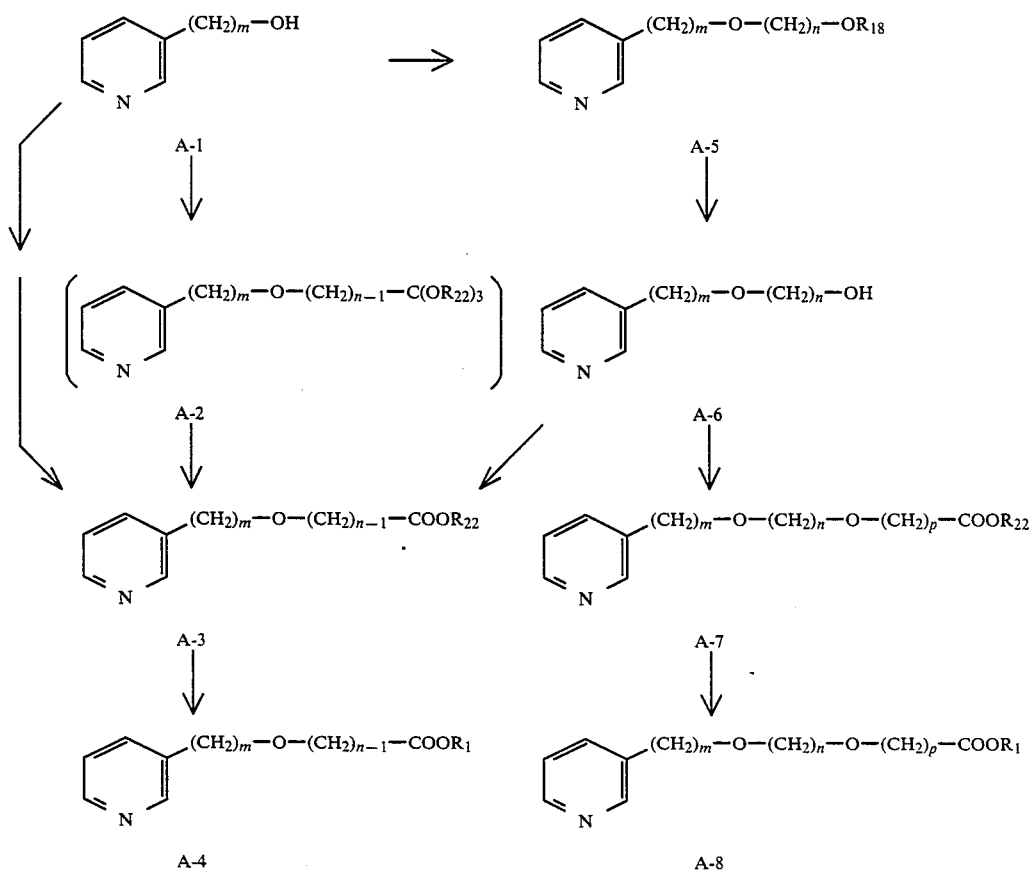

CHART B
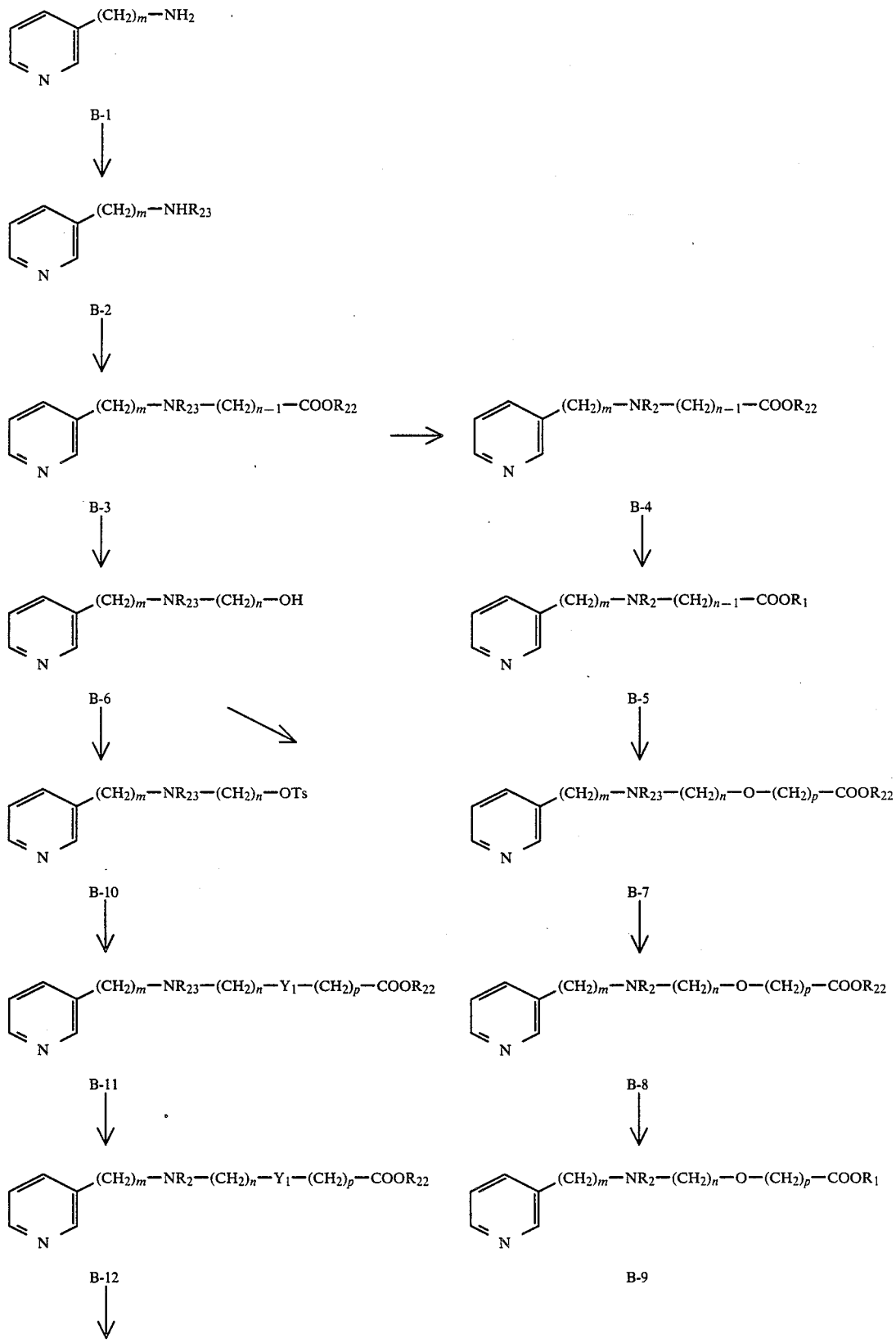

-continued
CHART B
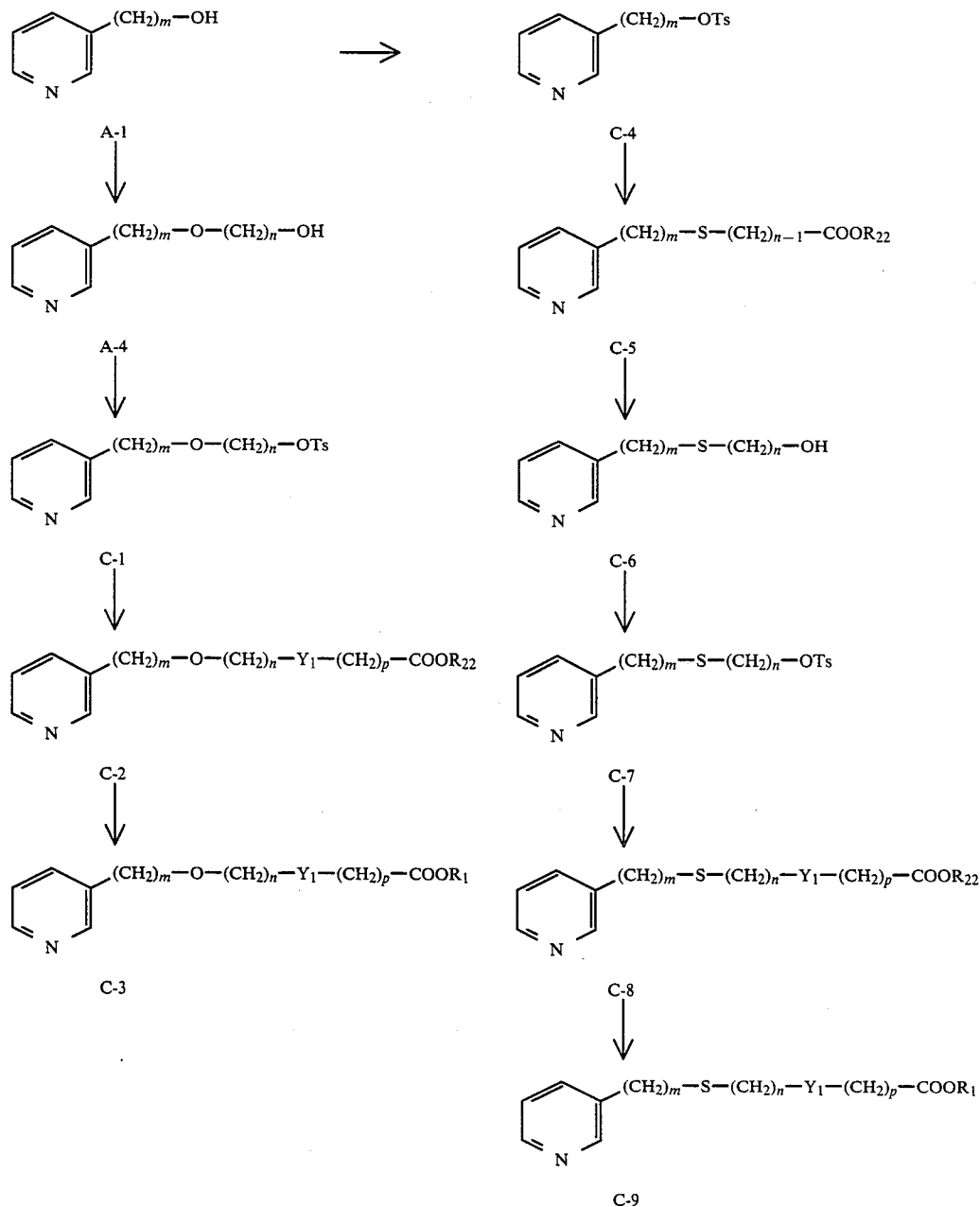
I claim:
1. A compound represented by the structural formula:

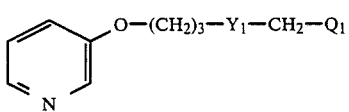
wherein $Y_1$ is
(a) —O— or
(b) —S—; and
wherein $Q_1$ is
(a) —CH$_2$CH$_3$, or
(b) —CO$_2$CH$_2$CH$_3$; and
pharmacologically acceptable salts thereof.
2. The compound of claim 1 which is 3-[3-(3-Pyridinyloxy)propoxy]-acetic acid, methyl ester.
3. The compound of claim 1 which is 3-[3-(3-Pyridinyloxy)propoxy]-acetic acid, sodium salt.
4. The compound is claim 1 which is [3-(3-Pyridinyloxy)-propane-1-thio]-acetic acid.
* * * * *